US005744495A

United States Patent [19]
Dagger et al.

[11] Patent Number: 5,744,495
[45] Date of Patent: Apr. 28, 1998

[54] N, N-DIETHYL-8, 8-DIPROPYL-2-AZASPIRO [4.5] DECANE-2-PROPANAMINE

[75] Inventors: Raymond E. Dagger, Warminster; Carolyn W. Grady, Philadelphia, both of Pa.

[73] Assignee: SmithKline Beecham Corporation, Philadelphia, Pa.

[21] Appl. No.: 679,480

[22] Filed: Jul. 12, 1996

Related U.S. Application Data

[60] Provisional application No. 60/016,065, Apr. 23, 1996 and provisional application No. 60/001,139 Jul. 13, 1995.

[51] Int. Cl.[6] ............................ A61K 31/40; C07D 209/54
[52] U.S. Cl. ............................................ 514/409; 548/408
[58] Field of Search ............................. 548/408; 514/409

[56] References Cited

U.S. PATENT DOCUMENTS

| | | | |
|---|---|---|---|
| 4,963,557 | 10/1990 | Badger et al. | 514/278 |
| 5,395,848 | 3/1995 | Bugelski et al. | 514/409 |
| 5,482,959 | 1/1996 | Badger | 514/409 |
| 5,534,522 | 7/1996 | Ando et al. | 514/299 |

FOREIGN PATENT DOCUMENTS

| | | |
|---|---|---|
| WO 92/02229 | 2/1992 | WIPO . |
| WO 92/14462 | 9/1992 | WIPO . |
| WO 94/04150 | 3/1994 | WIPO . |
| WO 95/03041 | 2/1995 | WIPO . |
| WO 95/03042 | 2/1995 | WIPO . |
| WO 95/03049 | 2/1995 | WIPO . |
| WO 95/16657 | 6/1995 | WIPO . |
| WO 96/03126 | 2/1996 | WIPO . |

OTHER PUBLICATIONS

J. Med. Chem. vol. 33, No. 11, pp. 2963–2970 (1990).

Primary Examiner—Mukund J. Shah
Assistant Examiner—Brenda Coleman
Attorney, Agent, or Firm—Pillsbury Madison & Sutro LLP

[57] ABSTRACT

An improved immumomodulatory agent, the dimaleate salt of N,N-diethyl-8,8-dipropyl-2-azaspiro[4.5]decane-2-propanamine.

4 Claims, No Drawings

N,N-DIETHYL-8,8-DIPROPYL-2-AZASPIRO[4.5]DECANE-2-PROPANAMINE

This application claims the benefit of U.S. Provisional Application Ser. No. 60/001,139, filed Jul. 13, 1995, and U.S. Provisional Application Ser. No. 60/016,065, filed Apr. 23, 1996.

This invention relates to an improved immunomodulatory agent, the dimaleate salt of N,N-diethyl-8,8-dipropyl-2-azaspiro[4.5]decane-2-propanamine. The compound is represented by Structure I:

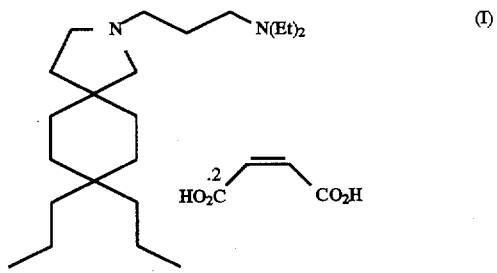

The compound of this invention is useful as an immunomodulatory agent, particularly in the treatment of rheumatoid arthritis.

DETAILED DESCRIPTION OF THE INVENTION

N,N-diethyl-8,8-dipropyl-2-azaspiro[4.5]decane-2-propanamine is a compound which is disclosed and claimed, along with pharmaceutically acceptable salts, hydrates and solvates thereof, as being useful as an immunomodulatory agent, particularly in the treatment of rheumatoid arthritis, in U.S. Pat. No. 4,963,557, the entire disclosure of which is hereby incorporated by reference. Particularly preferred among the pharmaceutically acceptable salts described in U.S. Pat. No. 4,963,557 and the only salt form prepared therein is the dihydrochloride salt. N,N-diethyl-8,8-dipropyl-2-azaspiro[4.5]decane-2-propanamine (hereinafter Compound A) and the dihydrochloride salt of Compound A (N,N-diethyl-8,8-dipropyl-2-azaspiro[4.5]decane-2-propanamine dihydrochloride—hereinafter Compound B) can be prepared by methods such as described in U.S. Pat. No. 4,963,557.

It has now surprisingly been found that the dimaleate salt form of Compound A (N,N-diethyl-8,8-dipropyl-2-azaspiro[4.5]decane-2-propanamine dimaleate—hereinafter Compound C) has numerous advantages over the dihydrochloride. The dimaleate, while being as highly soluble as the dihydrochloride, is more stable when stored in bulk prior to manufacture, particularly prior to tableting. The dihydrochloride is hygroscopic and thus picks up moisture upon storage. The lessened tendency toward hygroscopicity of Compound C is very important because the accuracy of weighing out bulk compound for manufacturing and analytical purposes, particularly for tableting purposes, would be affected if the compound's weight is partially attributable to water of hydration. Thus, constant assaying would be required to ensure that the proper amount of active drug is provided. Dose accuracy is particularly critical since the drug is effective in small dosages.

While Compound B is highly useful as an immunomodulatory agent, Compound C has the added advantages of ease of synthesis, lends itself to more accurate manufacturing procedures, particularly tableting procedures, and is far less hygroscopic which results in greater physical stability and greater ease of assaying drug content.

The compound of this invention, Compound C, is useful as an immunomodulatory agent, particularly in the treatment of rheumatoid arthritis. Compound C (active ingredient) can be administered in a conventional dosage form prepared by combining Compound C with a conventional pharmaceutically acceptable carrier or diluent according to known techniques, such as those described in U.S. Pat. No. 4,963,557. The route of administration may be oral, parenteral or topical. The term parenteral as used herein includes intravenous, intramuscular, subcutaneous, intranasal, intrarectal, intravaginal or intraperitoneal administration. The subcutaneous and intramuscular forms of parenteral administration are generally preferred. The daily oral dosage regimen will preferably be from about 0.01 to about 10 mg/kilogram of total body weight, most preferably from about 0.1 mg/kg to about 1 mg/kg. Preferably each oral dosage unit will contain the active ingredient in an amount of from about 0.1 mg to about 100 mg. The daily parenteral dosage regimen will preferably be from about 0.01 to about 10 mg per kilogram (kg) of total body weight, most preferably from about 0.1 to about 1 mg/kg. Preferably each parenteral dosage unit will contain the active ingredient in amount of from about 0.1 mg to about 100 mg. The daily topical dosage regimen will preferably be from about 1 mg to about 100 mg per site of administration. The above dosages relate to the preferred amount of N,N-diethyl-8,8-dipropyl-2-azaspiro[4.5]decane-2-propanamine expressed as the free base. It will be recognized by one of skill in the art that the optimal quantity and spacing of individual dosages of Compound C will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of Compound C given per day for a defined number of days, can be ascertained by those skilled in the art using conventional course of treatment determination tests.

Generally speaking, the compound of this invention is prepared by dissolving the base, N,N-diethyl-8,8-dipropyl-2-azaspiro[4.5]decane-2-propanamine, in an appropriate organic solvent, such as deoxygenated ethyl acetate, with subsequent addition of two or more equivalents of maleic acid. The compound of this invention is filtered off and dried in vacuo or air dried at an elevated temperature.

Maleic acid, 99%, is purchased from the Aldrich Chemical Company, Milwaukee, Wis.

The following examples further illustrate the present invention. The examples are not intended to limit the scope of the invention as defined hereinabove and as claimed below.

EXAMPLE 1

Preparation of N,N-diethyl-8,8-dipropyl-2-azaspiro[4.5]decane-2-propanamine Dimaleate

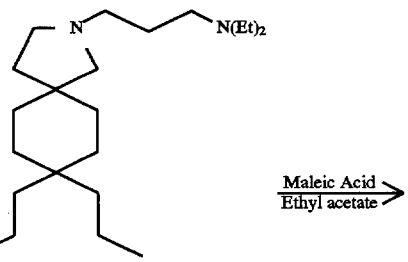

-continued

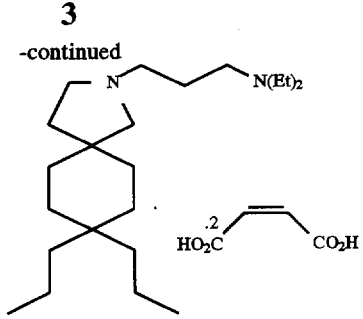

N,N-diethyl-8,8-dipropyl-2-azaspiro[4.5]decane-2-propanamine, 458 g of a crude oil containing residual solvent (89.1% by weight pure by HPLC analysis or 408 g, 1.21 mol of pure compound) was placed in a 12 L, 3-necked glass vessel under positive nitrogen pressure and equipped with an air driven stirrer and dissolved in deoxygenated ethyl acetate (6.9 L). Maleic acid (281.9 g, 2.43 mol) was added to the vigorously stirring solution. The slurry was stirred at ambient temperature for 3 hours then a white solid was filtered off. The white solid was washed with ethyl acetate (500 ml) and dried under high vacuum for 120 hours to yield 667 g (1.17 mol, 96.7%) of the title compound. This material was milled through a cone mill (Quadro) with an 18R sieve to yield 629.5 g (91.2%) of the title compound: mp 141°–142° C.; IR (KBr) 3400, 3100–3000, 3000–2800, 2679, 1646, 1584, 1504, 1386, 1367, 1194, 876, and 864 cm$^{-1}$; NMR (CDCl$_3$, 360 MHz) δ 0.88 (s, 6H), 1.18 (s, 8H), 1.26 (m, 4H), 1.33 (t, 6H, J=7.9, 10.9 Hz), 1.52 (m, 4H), 1.93 (t, 2H, J=10.0, 14.1 Hz), 2.32 (m, 2H), 3.19 (m, 6H), 3.30 (m, 2H), and 6.25 (s, 4H); $^{13}$C-NMR (CDCl$_3$, 360 MHz) δ 8.4, 14.9, 16.1, 20.7, 31.7, 32.5, 34.0, 35.2, 38.8, 42.3, 46.6, 48.7, 52.6, 52.9, 63.7, 135.7, and 169.3. Anal. Calcd for C$_{22}$H$_{44}$N$_2$—2(C$_4$H$_4$O$_4$) 63.35 C, 9.22 H, 4.93 N found 63.17 C, 9.28 H, 4.92 N.

The physical properties of Compound B and Compound C were compared.

EXAMPLE 2

Melting Points

The melting points of Compound B and Compound C are indicated in Table 1 below.

TABLE 1

| Compound B | 240–245° C. dec. |
|---|---|
| Compound C | 141–142° C. |

EXAMPLE 3

Hygroscopicity

The rate of moisture absorption of Compound B and Compound C were tested individually in an Integrated Microbalance System, MODEL MB 300 G (VTI Corporation, Hialeah, Fla.) using the accompanying Software Manual. The two compounds were analyzed under identical parameters, as indicated in Table 2(a) below. For comparison purposes the results of both compounds are summarized in Table 2(b) below.

TABLE 2(a)

Integrated Microbalance System set Up-Parameters for Compounds B and C.

| | |
|---|---|
| SAMPLE WEIGHT: | Approx 10 mg |
| DRYING TEMPERATURE: | 60° C. |
| HEATING RATE: | 10° C./min |
| EQUILIBRIUM CRITERIA, wt.: | 6 Ug |
| EQUILIBRIUM CRITERIA, % wg.: | 200% of wg |
| EQUILIBRIUM CRITERIA, time: | 240 min |
| SAMPLE INTERVAL: | 2 min |
| EXP. TEMPERATURE: | 25° C. |
| % Relative Humidity, start: | 10% |
| % Relative Humidity, max: | 100% |
| % Relative Humidity, step: | 5% |
| EQUILIBRIUM CRITERIA, wg.: | 6 Ug. |
| SAMPLE INTERVAL: | 2 min |
| DES. CUT-OFF: | 0% Relative Humidity |
| DATA COLLECTION INTERVAL: | 3 min. |

TABLE 2(b)

Moisture Absorption

| DATA POINT No. | % RELATIVE HUMIDITY | COMPOUND B % Weight Gain | COMPOUND C % Weight Gain |
|---|---|---|---|
| 1 | 0 | 0 | 0 |
| 2 | 10 | 0.20 | −0.21 |
| 3 | 15 | 1.81 | −0.18 |
| 4 | 20 | 2.17 | −0.08 |
| 5 | 25 | 2.84 | −0.12 |
| 6 | 30 | 3.74 | −0.08 |
| 7 | 35 | 3.15 | −0.08 |
| 8 | 40 | 3.30 | −0.08 |
| 9 | 45 | 4.74 | −0.05 |
| 10 | 50 | 5.49 | −0.04 |
| 11 | 55 | 9.07 | 0.04 |
| 12 | 60 | 9.26 | 0.1 |
| 13 | 65 | 9.50 | 0.18 |
| 14 | 70 | 15.47 | 0.41 |
| 15 | 75 | 31.30 | 0.56 |
| 16 | 80 | 36.53 | 0.89 |
| 17 | 85 | 44.16 | 1.70 |
| 18 | 90 | — | 5.37 |
| 19 | 95 | — | 42.88 |

EXAMPLE 4

Relative Solubilities

The solubilities of Compound B and Compound C were determined in three different systems: water, 0.1 HCl and methanol. The data are summarized in Table 3 below.

TABLE 3

| Solvent | Compound B mg/ml | Compound C mg/ml |
|---|---|---|
| Water | >100 | >100 |
| 0.1% HCl | >100 | >100 |
| methanol | >100 | >100 |

The present invention includes within its scope pharmaceutical compositions comprising Compound C, as the active ingredient, in association with a pharmaceutically acceptable carrier of diluent. The compound of this invention can be administered by oral or parenteral routes of administration and can be formulated in dosage forms appropriate for each route of administration including capsules, tablets, pills, powders and granules. In such solid dosage forms, the active compound is admixed with at least one inert diluent such as sucrose, lactose or starch. The oral dosage forms can also comprise, as is normal practice, addition substances other than inert diluents, e.g., lubricating agents such as magnesium stearate, glidants such as colloidal silicone dioxide, antioxidants such as butylated hydizoxy toluene. In the case of capsules, tablets and pills, the dosage forms may also comprise buffering agents. Tablets and pills can additionally be prepared for a sustained release or may be prepared with enteric coatings.

Preparations according to this invention for parenteral administration include sterile aqueous solutions although nonaqueous suspensions of emulsions can be employed. Such dosage forms may also contain adjuvants such as preserving, wetting, osmotic, buffering, emulsifying and dispersing agents. They may be sterilized by, for example, filtration through a bacteria retaining filter, by incorporating sterilizing agents into the compositions, irradiating the compositions or by heating the compositions.

The following examples further illustrate the pharmaceutical compositions which are a feature of this invention.

EXAMPLE 5

Tablet Composition

Lactose, microcrystalline cellulose, sodium starch glycolate, magnesium stearate and Compound C are blended in the proportions shown in Table 4 below. The blend is then compressed into tablets.

TABLE 4

| INGREDIENT | mg. |
| --- | --- |
| N,N-diethyl-8,8-dipropyl-2-azaspiro[4.5]decane-2-propanamine dimaleate | 8.45 |
| microcrystalline cellulose | 112 |
| lactose | 70 |
| sodium starch glycolate | 8 |
| magnesium stearate | 2 |

EXAMPLE 6

Injectable Parenteral Composition

An injectable form for administering Compound C is produced by stirring 5.0 mg. of N,N-diethyl-8,8-dipropyl-2-azaspiro[4.5]decane-2-propanamine dimaleate in 1.0 ml. of normal saline.

While the preferred embodiments of the invention are illustrated by the above, it is to be understood that the invention is not limited to the precise instructions herein disclosed and that the right to all modifications coming within the scope of the following claims is reserved.

What is claimed is:

1. The compound N,N-diethyl-8,8-dipropyl-2-azaspiro[4,5]decane-2-propanamine dimaleate, said dimaleate having a solubility in water 0.1% HCl and methanol similar to that of the corresponding dihydrochloride and a melting point lower than the dihydrochloride and being less hygroscopic and more stable in storage than the dihydrochloride.

2. A pharmaceutical composition comprising N,N-diethyl-8,8-dipropyl-2-azaspiro[4.5]decane-2-propanamine dimaleate and a pharmaceutically acceptable carrier or diluent.

3. A method of inducing immunomodulation which comprises administering an immunomodulatory effective amount of N,N-diethyl-8,8-dipropyl-2-azaspiro[4.5]decane-2-propanamine dimaleate to a patient in need of such treatment.

4. The method of claim 3 wherein the patient is in need of treatment for rheumatoid arthritis.

* * * * *